United States Patent [19]

Jiang et al.

[11] Patent Number: 5,261,937
[45] Date of Patent: Nov. 16, 1993

[54] SAMPLE CONCENTRATOR FILTER

[75] Inventors: Kenneth K. Jiang; Bernie B. Bernard, both of College Station, Tex.

[73] Assignee: O. I. Corporation, College Station, Tex.

[21] Appl. No.: 847,356

[22] Filed: Mar. 6, 1992

[51] Int. Cl.$^5$ .................................. B01D 53/04
[52] U.S. Cl. .............................. 96/101; 95/82; 73/23.41
[58] Field of Search .............. 95/67, 386, 270; 73/864.81, 864.85, 864.86, 864.87, 863.25, 23.41

[56] References Cited

U.S. PATENT DOCUMENTS

| | | | |
|---|---|---|---|
| 1,652,309 | 12/1927 | Kingdon | 55/410 |
| 2,800,977 | 7/1957 | Stewart | 55/523 |
| 2,920,716 | 6/1960 | Shada | 55/417 |
| 3,940,994 | 3/1976 | Klee et al. | 73/864.81 |
| 4,256,470 | 3/1981 | Zajicek et al. | 55/523 |
| 4,526,593 | 7/1985 | Myerson | 55/505 |

OTHER PUBLICATIONS

"Analysis of Volatile Organic Chemicals in Water Using the Ion Trap Detector TM (ITD TM )," by Jerry Thoma, Environmental Health Laboratories.
Volatile Organics Analysis: Building a State-of-the-Art Purge and Trap GC/Ms System, Reproduced from Alltech Environmental Update.
A Fully Automated Purge-and-Trap System for Analyzing Volatile Organics in Drinking Water, by J. S. Ho, P. Hodakievic, and T. A. Bellar.
The Determination of Volatile Organic Compounds from EPA Method 524.2 using Purge-and-Trap Capillary Gas Chromatography, ECD, and FID.
The analysis of volatile organics in drinking water with an OI 4460A purge and trap and an HP GC/Ms system, by Linda Doherty.
The Analysis of Volatile Organics in Drinking Water with OI 4460A Purge and Trap and an HP GC/MS System.
New 105m, Fused Silica HOCOL TM Column Provides Maximum Resolution of Volatile Compounds in Drinking Water, Reproduced from The Supelco Reporter, vol. IX, No. 4.
An Automated Purge-and-Trap System for Analyzing Volatile Organic Compounds in Drinking Water, by Allen K. Vickers.
Determination of Volatile Organics in Drinking Water with USEPA Method 524,2 and the the Ion Trap Detector.
Determination of Purgeable Halocarbons and Aromatics by Photoionization Hall Electrolytic Conductivity Detectors Connected in Series.

*Primary Examiner*—Charles Hart
*Attorney, Agent, or Firm*—Arnold, White & Durkee

[57] ABSTRACT

A filter for preventing foam and debris from accumulation on the trap used in sample concentration apparatus is disclosed. The filter is preferably a sintered metal frit removably inserted in the concentrator inlet on a sparge vessel. The filter also serves as a check valve for preventing water vapor or residual analytes in the sparge vessel from contaminating dry gas or other external samples which pass through the concentrator inlet.

8 Claims, 2 Drawing Sheets

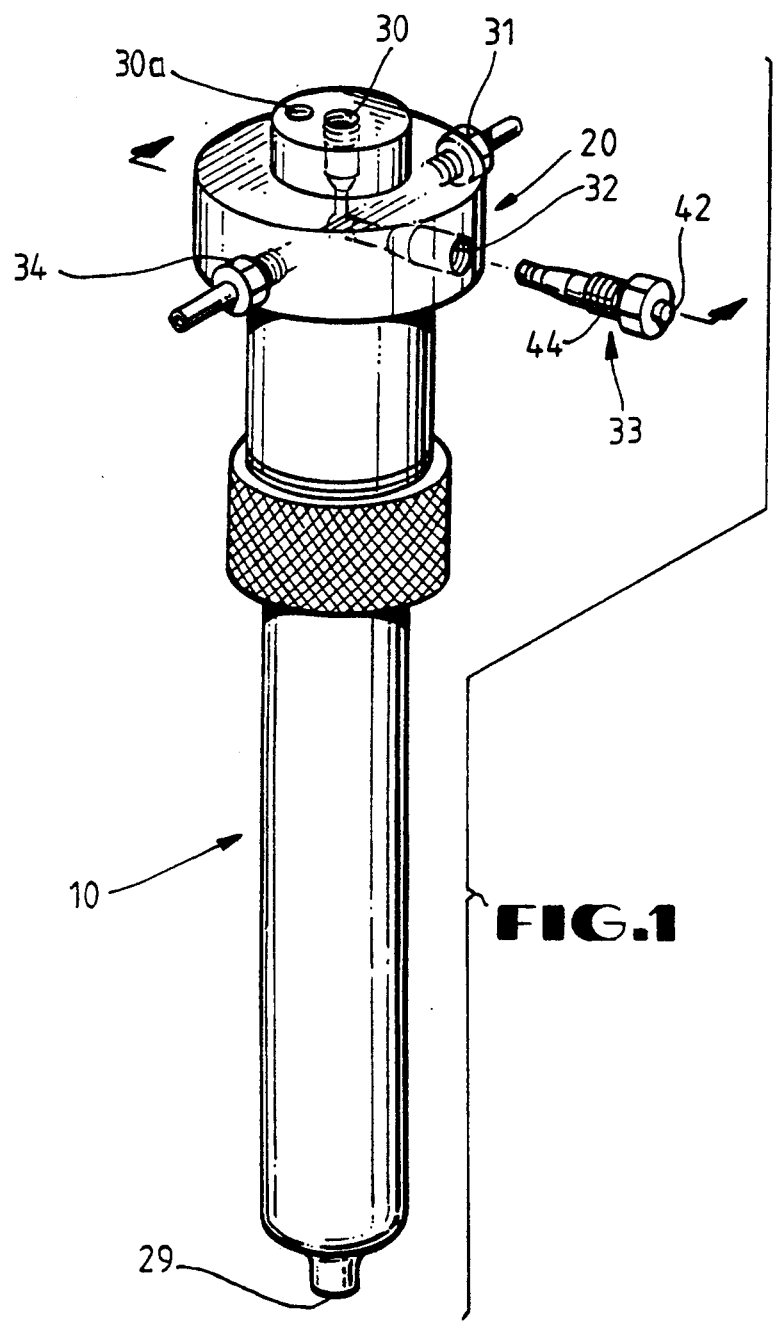
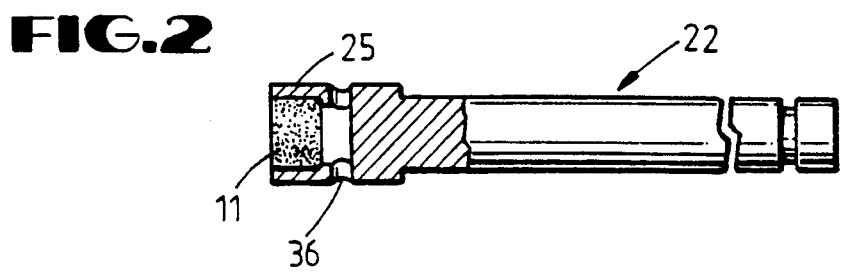

SAMPLE CONCENTRATOR FILTER

BACKGROUND OF THE INVENTION

1. Field of the Invention

The present invention relates generally to sample concentration for analyzing volatile organic compounds in air, water and soils. More specifically, the present invention relates to a filter for a sample concentrator to reduce accumulation of foam and debris during purging of an inert gas through aqueous solution.

2. Related Art

Sample concentrators are used in purge-and-trap, headspace, and thermal desorption gas chromatography ("GC") analysis. Purge-and-trap GC technique has been used for analyzing volatile organics in water since approximately the early 1970's. In 1987 the U.S. Environmental Protection Agency ("EPA") promulgated national primary drinking water regulations for certain volatile organic chemicals ("VOCs"). The EPA also proposed maximum contamination levels for eight volatile organic chemicals. These regulations require the use of the purge-and-trap GC technique. In addition to the eight regulated volatile organic chemicals, the EPA also promulgated monitoring requirements for an additional 52 synthetic volatile organic chemicals.

The EPA has approved certain analytical methods for analyzing these 60 compounds. One of the methods is 502.2, a purge-and-trap capillary-column GC method using a photoionization detector and an electrolytic conductivity detector joined in series. A second method is method 524.2, a purge-and-trap capillary-column GC-MS method.

Purge-and-trap systems for analyzing VOCs in drinking water have been assembled from a variety of equipment typically including a purging device, trap, and desorber. These systems also are referred to as sample concentrators. The purge-and-trap system or sample concentrator interfaces to a GC capillary column, then with a photoionization detector/electrolytic conductivity detector or a mass-spectrometer. These components are interconnected via pneumatic conduits.

Highly volatile organic compounds with low water solubility are extracted (purged) from the sample matrix by bubbling an inert gas (i.e., helium or nitrogen) through a five milliliter aqueous sample. Purged sample components are trapped in a tube containing suitable sorbent materials. When purging is complete, the sorbent tube is heated and backflushed with the inert gas to desorb trapped sample components onto a capillary GC column. The column is temperature programmed to separate the method analytes which are then detected with a photoionization detector (PID) and a halogen specific detector placed in series, or with a mass spectrometer.

Tentative identifications are confirmed by analyzing standards under the same conditions used for samples, and comparing results and GC retention times. Additional confirmatory information can be gained by comparing the relative response from the two detectors. Each identified component is measured by relating the response produced for that compound to the response produced by a compound that is used as an internal standard. For absolute confirmation, the gas chromatography/mass spectrometry (GC/MS) determination according to method 524.1 or method 524.2 may be used.

As stated above, the typical purge and trap system consists of the purging device, trap, and desorber. Systems are commercially available from several sources that meet EPA specifications.

Under EPA specifications, the glass purging device must be designed to accept five to twenty-five ml. samples with a water column at least 5 cm. deep. Gaseous volumes above the sample are kept to a minimum to reduce "dead volume" effects. The purged gas passes through the water column as finely divided bubbles.

The sorbent trap is a tube typically at least 25 cm. long and having an inside diameter of at least 0.105 inches. The trap contains certain sorbent materials which the EPA has specified as 2,6-diphenylene oxide polymer, silica gel, and coconut charcoal. The EPA regulations specify the ratios of the adsorbent material. The desorber must be capable of rapidly heating the trap to 180° C.

The model 4460A sample concentrator manufactured by OI Analytical of College Station, Texas, is an example of a purge and trap, or sample concentrator, device. The model 4460A is a microprocessor controlled device that stores method 502.2 and 524.2 operating conditions as default parameters. Operating conditions may be changed by the user to accommodate other types of purge and trap analysis.

In addition to purge-and-trap methods and analyses, sample concentration gas chromatography is used in headspace analysis of liquids and solids, and in thermal desorption analysis of air tube samples. Headspace and thermal desorption techniques are not only used for environmental analyses, but also for clinical and industrial applications.

Typically, a sparge vessel includes a concentrator inlet at the open end thereof. The concentrator inlet is a manifold that includes a plurality of fittings: for purge gas, for an external sampler, and for dry gas. For example, dry gas may be introduced through the manifold and directed to the trap for drying out the trap. The concentrator inlet also includes sample introducing means. Valves may be provided for selectively directing the gas or analytes from the sparge vessel or inlet fitting to an outlet fitting which is connected to a conduit leading to the sorbent trap.

As discussed above, VOCs are purged from the water sample by bubbling an inert gas, such as helium, through a 5 ml aqueous sample. Typically, the sample is contained in a glass sparge vessel.

One of the problems encountered in transferring the gas/analyte from the sparge vessel to the trap is foaming of samples. Because of the bubbling helium gas, surfactant on the sample surface may be propelled out from the sparge vessel and carried into the trap. Liquid foam and particles have deleterious effects on the trap. Therefore, it is necessary to frequently replace traps due to accumulation of foam and debris that is propelled from the sparge vessel. Eventually, the liquid foam and particles cake on the trap with adverse effects on the detection of analytes.

SUMMARY OF THE INVENTION

The present invention overcomes the above-mentioned problems and disadvantages by providing a filter for preventing foam and debris leaving the sparge vessel from entering the trap. According to the present invention, the filter is preferably a sintered metal frit removably inserted in the concentrator inlet on a sparge vessel. The filter also serves as a check valve for preventing water vapor or residual analytes in a sparge vessel from contaminating dry gas or other external samples which pass through the concentrator inlet. The filter acts as a vapor barrier as a result of a pressure drop across the filter.

BRIEF DESCRIPTION OF THE DRAWINGS

FIG. 1 is a perspective view of a concentrator inlet and a part of a sparge vessel used with the present invention.

FIG. 2 is a section view of the filter retainer and filter according to a preferred embodiment of the present invention.

DETAILED DESCRIPTION OF A PREFERRED EMBODIMENT

Figure 3:
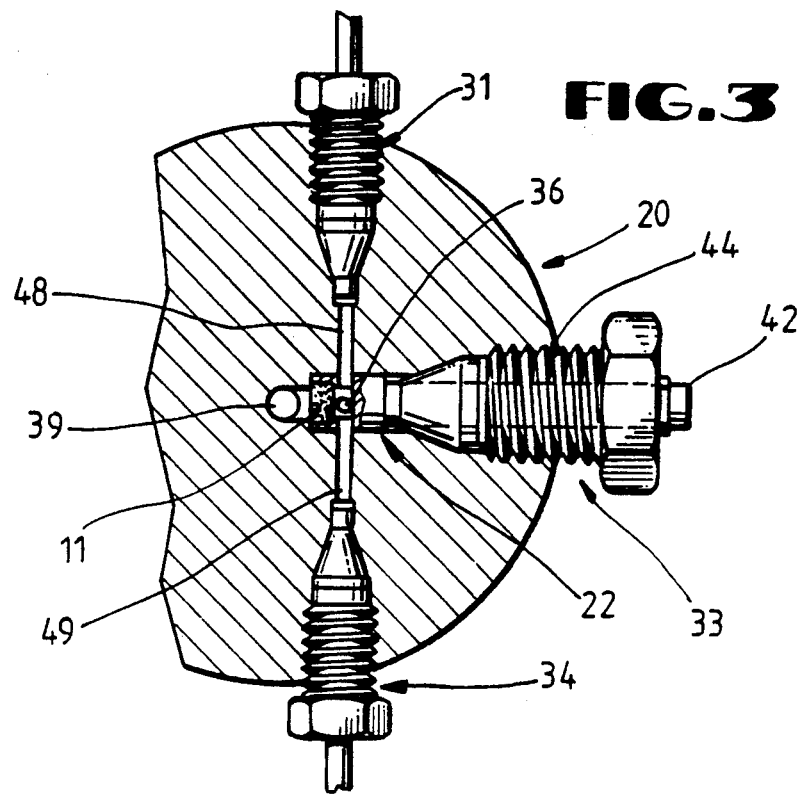
FIG. 3 is a top view, in section of the manifold and inlets according to a preferred embodiment of the present invention.
Figure 4:
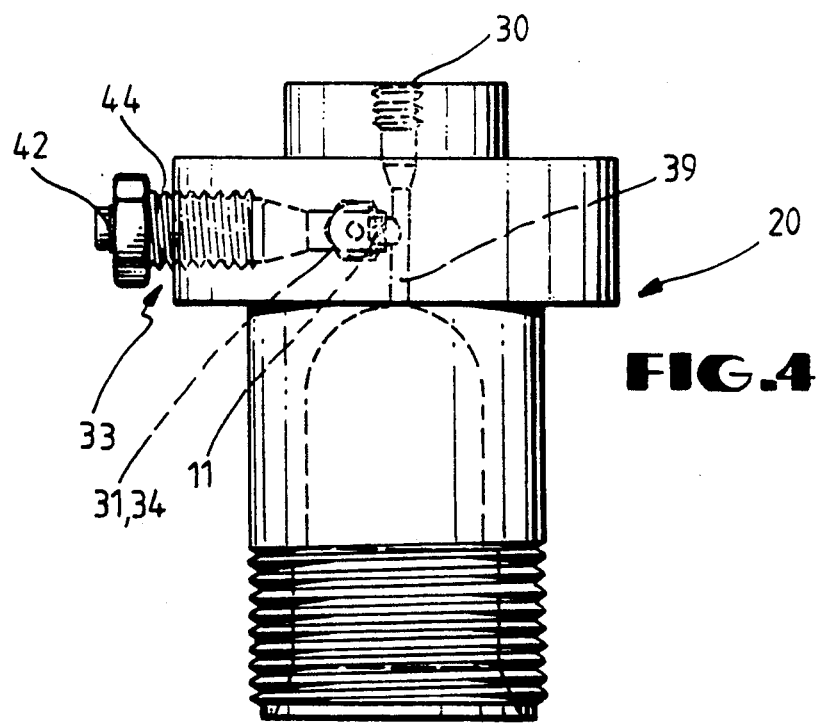
FIG. 4 is a cross-sectional elevation of FIG. 1 with the closure and filter device in an enlarged view.

As shown in FIG. 1, the present invention may be used with a sparge vessel 10 having a concentrator inlet or manifold 20 on the open end thereof. The manifold has a plurality of fittings. The fittings are designed to engage threaded inlets/outlets. Typically, the manifold includes thermocouple/water sample delivery inlets 30,30a, dry gas inlet fitting 31, and external sampler inlet fitting 32. The sample may be introduced through inlet 30 with a needle (not shown).

The manifold also includes an outlet fitting 34 connected to the trap (not shown). As is conventional in sample concentration, purge gas is introduced into the sparge vessel through inlet 29, then passes through the sample. The purge gas/analyte stream then flows through passage 39, passage 49, and outlet fitting 34 to the trap.

As shown in FIG. 2, the present invention involves a filter for filtering foam and other debris from the purge gas/analyte stream when it reaches the manifold, before reaching the trap. The filter 11 preferably is a sintered metal frit having porosity sufficient for filtering particles and foam that is produced during purging of the sparge vessel. Generally, nickel may be used for the frit. In a preferred embodiment, the filter has a pore size of 40 microns. It is desirable that the pore size achieve an optimum balance between filtering action and the pressure drop across the filter, as will be explained in more detail below.

In a preferred embodiment, the filter 11 is positioned in the manifold 20. To provide easy access and removability, the filter 11 is in the nose 25 of filter retainer 22. The filter retainer is positioned in filter retainer body 33 having an externally threaded surface 44 that is threadable into external sample inlet fitting 32. During purging of the sample from sparge vessel 10, tubing 42 in the filter retainer body is blocked or provided with a normally closed valve.

During purging of the sample from sparge vessel 10, the purge gas/analyte stream flows from passage 39 through filter 11, orifice 36 in the filter retainer, and through passage 49 to outlet fitting 34. During this purge process, the dry gas inlet and external sampler inlet are normally closed or sealed by valves or other means as is well known to those skilled in the art.

However, at times it is desirable to introduce dry gas to the same trap, without first disconnecting sparge vessel 10 and/or manifold 20. When dry gas is introduced to the trap, i.e. from inlet 32, passage 48, passage 49, and outlet 34, the filter 11 acts as a check valve to prevent water vapor and/or other residual analytes in the sparge vessel 10 from contaminating dry gas flow between inlet 32 and outlet 34. The pressure drop across the filter is sufficient to prevent water vapor and other residual analytes in the sparge vessel from passing through the filter 11.

Similarly, an external sampler may be connected to the trap without removal of the sparge vessel and/or manifold 20. The flow path of the external sample is from inlet 33, passage 50, passage 49, to outlet 34. For this flow path the filter retainer body is opened. As discussed above, the filter acts as a check valve to prevent water vapor and/or other residual analytes in the sparge vessel 10 from contaminating the external sample flow between inlet 33 and outlet 34.

When an external sample is used, the filter retainer body may be removed from inlet 32 and replaced with an external sample connection (not shown). The construction of the external sample connection may be virtually identical to the filter retainer body, however the tubing 42 is open for flow of the external sample. In the external sample connection, the filter 11 may be replaced with a solid element in the nose portion.

Thus, the present invention provides means of connection of dry gas and/or external samples to the trap through the same concentrator inlet or manifold.

Additionally, the filter of the present invention eliminates the need for a separate valve between the sparge vessel and the trap outlet, as the pressure drop across the filter acts as a check valve.

Another advantage of the present invention is that the filter prevents water vapor and residual analytes from the sparge vessel from contaminating dry gas or analytes from external samples to be introduced to the trap.

Another advantage of the present invention is filtering foam, particles and debris from the analyte stream before it reaches the trap.

Yet another advantage of the present invention is providing an easily replaceable and removable filter for the sample concentrator inlet.

The filter of the present invention enhances the detection of analytes in a GC. The filter of the present invention also reduces replacement of the sorbent trap.

Although variations in the embodiment of the present invention may not each realize all the advantages of the invention, certain features may become more important than others in various applications of the device. The invention, accordingly, should be understood to be limited only by the scope of the appended claims.

What is claimed is:

1. A filtering device for use with a sparge vessel in a purge-and-trap system, the sparge vessel having an opening at one end thereof, comprising:
   (a) a closure attached to cover the opening of the sparge vessel, the closure having a first flow path communicating with the interior of the sparge vessel and at least one second flow path intersecting the first flow path;
   (b) a filter positioned in the first flow path adjacent the intersection of the first and second flow paths; and
   (c) a filter retainer removably connected to the closure and closing at least one of the second flow paths, the filter retainer having a first end insertable into the first flow path, a longitudinal outer surface positionable at the intersection of the first and second flow paths, a cavity in the first end for holding the filter in the first flow path, and at least one passage between the cavity and the longitudinal outer surface, the filter retainer retractable to remove the filter from the first flow path without disassembly of the filter from the filter retainer.

2. The filtering device of claim 1 wherein the cavity further comprises an internal shoulder, the filter configured to abut the internal shoulder, the passage located interiorly of the shoulder.

3. The filtering device of claim 1 wherein the filter retainer is threaded to the closure.

4. The filtering device of claim 1 wherein the filter retainer is a cylindrical member and the passage extends radially between the cavity and the cylindrical outer surface.

5. The filtering device of claim 1 wherein the filter and filter retainer are removable from the flow path as a unit.

6. A manifold for the opening of a sparge vessel, comprising:
 (a) a manifold body covering the opening of the sparge vessel and having a first internal passage communicating with the interior of the sparge vessel, a second internal passage transverse to the first internal passage and communicating between the first internal passage and the exterior of the body, and at least one third internal passage transverse to the second internal passage and communicating between the second internal passage and the exterior of the manifold body;
 (b) a filter retaining member having a hollow nose portion, an outer surface and an orifice communicating between the hollow nose portion and the outer surface remote from the hollow nose portion, the filter retaining member insertable into and closing the second internal passage such that the orifice communicates between the second and third internal passages; and
 (c) a metal frit positionable in the nose portion such that the metal frit restricts flow between the first internal passage and the second or third internal passages.

7. The manifold of claim 6 wherein the filter retaining member is retractable from the second internal passage without interrupting flow between the first and third internal passages.

8. A filter assembly for removal of foam and particles from an aqueous sample purged from a sparge vessel, comprising:
 (a) a manifold having an inlet passage intersecting a plurality of outlet passages, the manifold connectable to the opening of the sparge vessel in sealed relation therewith;
 (b) a filter chamber between the inlet passage and the plurality of outlet passages;
 (c) a metal frit insertable into the filter chamber; and
 (d) a filter retainer adapted to close one of the outlet passages and having a first end, a lateral outer surface, and at least one orifice communicating between the first end and the outer lateral surface, the first end configured to retain the frit in the filter chamber such that the purged sample enters the manifold through the inlet passage, passes through the frit and said at least one orifice, and exists the manifold through at least one of the plurality of outlet passages.

* * * * *